United States Patent [19]
Hirschman

[11] Patent Number: 5,807,839
[45] Date of Patent: Sep. 15, 1998

[54] METHOD FOR STIMULATING RED BLOOD CELL PRODUCTION

[75] Inventor: Shalom Z. Hirschman, Riverdale, N.Y.

[73] Assignee: Advanced Viral Research Corp., Hallandale, Fla.

[21] Appl. No.: 835,797

[22] Filed: Apr. 15, 1997

[51] Int. Cl.$^6$ .......................... A61K 31/395; C07H 21/00
[52] U.S. Cl. .................................. 514/44; 514/2; 514/21; 514/814
[58] Field of Search .................................. 514/44, 2, 21, 514/814

[56] References Cited

PUBLICATIONS

Reynolds, Margaret R., Generalized Vaccinia, Symposium, pp. 5–6, 1960.
Kuckku, Morris E., Herpetic Diseases, Symposium, pp. 7–13, 1960.
Schaeffer, Oden A., Influenza, Symposium, pp. 15–21, 1960.
Seydel, Frank, Epidemic, Asian Influenza, Symposium, pp. 23–34, 1960.
Cooke, Stanford B., Upper Respiratory Viral Manifestations, Clinical Symposium on Viral Diseases Demonstrating the Anti–viral Biotic Properties of the Drug Reticulose (Symposium), Sep., 1960, Miami Beach, Florida, pp. 25–32.
Medoff, Lawrence R., Infectious Mononucleosis, Symposium, pp. 33–37, 1960.
Anderson, Robert H., Encephalitis, Symposium, pp. 39–52, 1960.
Plucinski, Stanisloff J., Suspected Viral Varieties, Symposium, pp. 53–59, 1960.
Kosaka, K. and Shimada, Y., Infectious Hepatitis, Symposium, pp. 61–74, 1960.
Anderson, Robert H. and Thompson, Ralph M., Treatment of Viral Syndrome with a Lipoprotein–Nucleic Acid Compound (Reticulose), A Report of Five Cases, Virginia Medical Monthly, 84: 347–353, 1957.
Reynolds, Margaret R., Generalized Vaccinia Successfully Treated with Lipoprotein–Nucleic Acid Complex (Reticulose), Archives of Pediatrics, 77:421–422, 1960.
Wegryn, Stanley P., Marks, Robert A. and Baugh, John R., Herpes Gestationis, A Report of 2 Cases, American Journal of Obstetrics and Gynecology, 79:812–814, 1960.
Catterall, R.A., Lumpur, Kuala, A New Treatment of Herpes Zoster, Vaccinia and Chicken Pox, J. Roy. Coll. Gen. Practit., 1970, 19,182.
Chinnici, Angelo A., Reticulose in Treatment Aids patients, Personal Communication to William Bregman, Jul. 6, 1992.
Cott, Rafael A., Summary of 11 Cases of Viral Infections Treated with Reticulose, Private Communication with Advance Viral Research Corp., 1989.
Cohen, Matthew, The Efficacy of a Peptide–Nucleic Acid Solution (Reticulose) for the Treatment of Hepatitis A and Hepatitis B—a Preliminary Controlled Human Clinical Trial, J. Roy. Soc. Health, Dec., 1992, 266–270.
Mundschenk, David D., In Vitro Antiviral Activity of Reticulose vs Influenaz A, Personal Communication with William Bregman, May 1, 1990.
Resnick, Lionel, Anti–HIV in Vitro Activity of Two Samples of Peptide–nucleic Acid Solution, Personal Communication with Dr. Bernard Friedland, Dec. 22, 1989.
Friedland, Bernard, In Vitro Antiviral Activity of a Peptide––Nucleic Acid Solution Against the Human Immunodeficiency Virus and Influenza A Virus, J. Roy. Soc. Health, Oct. 1991, 170–171.
Brazier, Anne D., Method for in Vitro Antiviral Evaluation Human Immunodeficiency Virus (HIV), Personal Communication with Dr. Bernard Friedland, Oct. 4, 1989.
Behbehani, Abbas M., Haberman Sol and Race, Geroge J, The Effect of Reticulose on Viral Infections of Experimental Animals, Southern Medical Journal, Feb., 1962, 185–188.
Treatment of Viral Diseases with A Lipo–protein Nucleic Acid Complex (Reticulose)—A Clinical Study, Scientific Exhibit: Virginia State Medical Society Meeting, Washington D.C., Nov., 1957.
Kempe, Henry C., Fulginiti, Vincent A., and Vincent, Leone St., Failure to Demonstrate Antiviral Activity of Reticulose, Diseases of Children, vol. 103, No. 5, 655–657, 1962.
Sanders, Murray, Controlled Animal Studies with Reticulose Illustrating the Interference of Lipoprotein–Nucleic Acid Complex in the Experimental Animal Infected with Human Pathogenic Viral Entities, Southern Medical Association Scientific Exhibit, Dallas, Texas, Nov., 1961.

*Primary Examiner*—Dian C. Jacobson
*Attorney, Agent, or Firm*—Cohen, Pontani, Lieberman & Pavane

[57] ABSTRACT

The present invention discloses a method for treating anemia by stimulating red blood cells production by administering parenterally Product R, a peptide-nucleic acid preparation.

20 Claims, No Drawings

METHOD FOR STIMULATING RED BLOOD CELL PRODUCTION

BACKGROUND OF THE INVENTION

I. Field of the Invention

The present invention relates to a method for using Product R as hereinafter defined to stimulating productions of red blood cells.

II. Description of the Related Art

All mammals possess a hematopoietic (blood forming) system that replenishes the multiplicity of blood cell types found in a healthy animal, including white blood cells, clot forming cells and red blood cells (erythrocytes). In the adult mammal the primary site of hematopoiesis is the bone marrow.

The bone marrow, if considered as a single tissue, is the largest tissue of the body. In the average human adult the total weight of the bone marrow is about 3 kg. Marrow fills the central core of nearly all bones. Bone marrow has three types of tissue; vascular tissue, adipose tissue and the tissue directed to hematopoiesis or blood cell formation. The vascular tissue is the circulatory system that supplies nutrients and removes wastes from the actively growing cells. The hematopoietic tissue is responsible for the formation of erythrocytes, platelets, granulocytes and monocytes, and lymphocyte precursors. Adipose tissue consists of fat cells which contribute little to the function of the bone marrow.

Maturation and differentiation of specialized subsets of blood cells takes place in the thymus, spleen, lymph nodes and gut-associated lymphoid tissues. Current scientific understanding proposes that small amounts of specific hematopoietic growth factors direct the proliferation, differentiation, and maturation of each of the various hematopoietic cell types from a small population of pluripotent hematopoietic stem cells. These various growth factors act at different times on different cell populations, ultimately giving rise to a functional hematopoietic system.

One specific and vital role of the mammalian hematoietic system is the production of erythrocytes, or red blood cells, which transport oxygen to the various tissues of the animal's body. The process of producing erythrocytes (erythropoiesis) occurs continuously throughout an animal's life span to offset erythrocyte destruction. The typical red blood cell has a relatively short life-span, usually 100 to 120 days. Erythropoiesis is a precisely controlled physiological mechanism whereby sufficient numbers of erythrocytes are produced to enable proper tissue oxygenation, but not so many as to impede circulation.

All peripheral blood cells arise from a common progenitor cell known as the pluripotent hemopoietic stem cell. An important property of stem cells is self-renewal, which ensures a continuous supply throughout the lifetime of the individual. When required, a pluripotent cell can begin to differentiate, and with successive divisions it loses the capacity for self-renewal, and its progeny becomes committed to a particular line of development. These progenitors will then give rise to all the blood cells capable of functional purposes.

The formation of mature blood cells comes at the end of a process which comprises the proliferation and maturation of specifically committed progenitor cells from each lineage. Pluripotent cells from each lineage are thus capable of producing a clone consisting of a number of red cells, granulocytes, platelets and lymphocytes, together with their intermediate progenitor cells.

Under normal circumstances, the marrow is able to respond quickly to an increased demand for a particular type of cell. How it does so is the subject of much current research. It is known that the process of proliferation and differentiation of progenitor cells is under the control of several growth stimulants known as hematopoietic hormones, e.g. erythropoietin (EPO) and several colony-stimulating factors.

Erythropoiesis consists of a process that begins at the stage of early BFU-E (burst-forming unit—erythroid, the earliest red cell precursor) formation, mainly governed by interleukin-3 (IL-3) and subsequently further maturation to CFU-E (colony-forming unit erythroid) and normoblasts by erythropoietin (EPO). Normoblasts mature to reticulocytes and then to erythrocytes, the mature blood cells.

Erythropoiesis is now known to be primarily controlled by EPO, an acidic glycoprotein. The EPO stimulates the production of new erythrocytes to replace those lost to the aging process. Additionally, EPO production is stimulated under conditions of hypoxia, wherein the oxygen supply to the body's tissues is reduced below normal physiological levels despite adequate perfusion of the tissue by blood. Hypoxia may be caused by hemorrhaging, radiation-induced erythrocyte destruction, various anemias, high altitude, or long periods of unconsciousness. In response to tissues undergoing hypoxic stress, EPO will increase red blood cell production by stimulating the conversion of primitive precursor cells in the bone marrow into proerythroblasts which subsequently mature, synthesize hemoglobin and are released into the circulation as red blood cells.

Certain disease states involve abnormal erythropoiesis. Recombinant human EPO is being used therapeutically in treating anemia associated with end-stage renal disease. Patients undergoing hemodialysis to treat this disorder typically suffer severe anemia, caused by the rupture and premature death of erythrocytes as a result of the dialysis treatment. EPO is also useful in the treatment of other types of anemia. For instance, chemotherapy-induced anemia, anemia associated with myelodysplasia, those associated with various congenital disorders, AIDS-related anemia, and prematurity-associated anemia, may be treated with EPO. Additionally, EPO may play a role in other areas, such as helping to more quickly restore a normal hematocrit in bone marrow transplantation patients, in patients preparing for autologous blood transfusions, and in patients suffering from iron overload disorders.

Product R[1] emerged as an antiviral product in the 1930's. While it was originally believed to be a product composed of peptone, peptides and nucleic acids (fully defined hereafter), the precise composition remains unidentified. Nevertheless, Product R has demonstrated an ability to inhibit rapidly the course of several viral diseases. It is nontoxic, miscible with tissue fluids and blood sera and free from anaphylactogenic properties.

Insofar as the applicant knows, Product R has never been suggested for performing a similar function to that performed by EPO. It has now been discovered that Product R is useful in stimulating red blood cell production, therefore in treating patients suffering from severe anemia resulting from chronic renal failure, radiation, chemotherapy or AIDS.

SUMMARY OF THE INVENTION

Accordingly, an object of the present invention is to provide a method comprising the parenteral administration of Product R for stimulating red blood cell production.

Another object of the present invention is to provide a method for treating patients suffering from anemia resulting from chronic renal failure, radiation, chemotherapy or AIDS.

Specifically, Product R is administered parenterally to the patients in a range from about 5 microliters to about 40 microliters per kilogram of the patient's body weight per day in a sterile injectable formulation.

DETAILED DESCRIPTION OF THE PRESENTLY PREFERRED EMBODIMENTS

As used herein, Product R is the product produced according to either of the following methods.

Method I For Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3° to 7° C. in a suitable container and gently stir until all the ingredients have been properly wet. Carefully add while stirring about 16.5 g of sodium hydroxide (reagent grade ACS) and continue stirring until sodium hydroxide completely dissolved. Autoclave at about 9 lbs pressure and 200°–230° F. for a period of time until RNA is completely digested, for example, about 4 hours. At the end of the period, the autoclave is stopped and the reaction flask and contents are permitted to slowly cool to ambient temperature. Then cool for at least six hours at about 3°–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/ml, the final volume is approximately 5 liters. The pH is then adjusted with either concentrated HCl (reagent grade ACS) or 1.0 normal NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclave for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

Method II For Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3° to 7° C. in a suitable container and gently stir until all the ingredients have been properly wet. Slowly add while stirring about 11.75 ml of hydrochloric acid (reagent grade ACS) and continue stirring until hydrochloric acid is completely dissolved. Autoclave at about 9 lbs pressure and 200°–230° F. for a period of time until RNA is completely digested, for example, about 4 hours. At the end of the period, the autoclave is stopped and the reaction flask and contents are permitted to slowly cool to ambient temperature. Then cool for at least six hours at about 3°–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/ml, the final volume is approximately 5 liters. The ph is then adjusted with either concentrated HCL (reagent grade ACS) or 35% (w/v) of NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclave for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

For the above stimulation of red blood cell production, which is therefore useful for treating anemia such as anemia resulting from chronic renal failure, radiation therapy, chemotherapy or AIDS, a suitable effective dose of Product R is in the range from about 2.5 microliters to about 40 microliters per kilogram of body weight per day, preferably in the range of about 5 microliters to about 25 microliters per kilogram of body weight per day. Most preferably Product R is administered in an amount of about 15 microliters per kilogram of body weight per day for two weeks and then 7.5 microliters per kilogram of body weight per day thereafter. The desired dose may be administered as two, three or more sub-doses at appropriate intervals, generally equally spread in time, throughout the day. Preferably, the full daily dose is administered in one administration.

Product R may be administered by any suitable injection route including, but not limited to intravenously, intraperitoneally, subcutaneously, intramuscularly, and intradermally, etc. The presently preferred route of administration is subcutaneously. It will be appreciated that the preferred route may vary with, for example, the condition and age of the recipient.

While it is possible for Product R to be administered as part of a pharmaceutical formulation, it is preferable to present it alone, although it may be administered at about the same time as one or more other pharmaceuticals are independently administered. If Product R is administered as part of a pharmaceutical formulation, the formulations of the present invention comprise at least one administered ingredient, as above defined, together with one or more acceptable carriers thereof and optionally other therapeutic ingredients. The carrier(s) must be "acceptable" in the sense of being compatible with the other ingredients of the formulation and not deleterious to the recipient thereof.

The formulations may conveniently be presented in unit-dose or multi-dose containers, e.g. sealed ampules and vials.

Preferred unit dosage formulations are those containing a daily dose or unit, daily sub-dose, or an appropriate fraction of the administered ingredient.

The above method for stimulating red blood cell production may be used to treat patients suffering from various forms of anemia such as anemia caused by chronic renal failure, radiation therapy, chemotherapy or AIDS.

Thus, while there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. A method for stimulating red blood cell production, comprising administering parenterally to a patient an effective treatment amount of Product R in a sterile injectable formulation.

2. The method of claim 1 wherein said Product R is administered in a range from about 2.5 microliters to about 40 microliters per kilogram of body weight per day.

3. The method of claim 1 wherein said Product R is administered in a range from about 5 microliters to about 25 microliters per kilogram of body weight per day.

4. The method of claim 1 wherein said Product R is administered in amount of about 15 microliters per kilogram of body weight per day for two weeks, and then 7.5 microliters per kilogram of body weight per day thereafter.

5. A method for treating a patient suffering from anemia resulting from chronic renal failure, comprising administering parenterally to said patient an effective treatment amount of Product R in a sterile injectable formulation.

6. The method of claim 5 wherein said Product R is administered in a range from about 2.5 microliters to about 40 microliters per kilogram of body weight per day.

7. The method of claim 5 wherein said Product R is administered in a range from about 5 microliters to about 25 microliters per kilogram of body weight per day.

8. The method of claim 5 wherein said Product R is administered in amount of about 15 microliters per kilogram of body weight per day for two weeks, and then 7.5 microliters per kilogram of body weight per day thereafter.

9. A method for treating a patient suffering from anemia resulting from radiation therapy, comprising administering parenterally to said patient an effective treatment amount of Product R in a sterile injectable formulation.

10. The method of claim 9 wherein said Product R is administered in a range from about 2.5 microliters to about 40 microliters per kilogram of body weight per day.

11. The method of claim 9 wherein said Product R is administered in a range from about 5 microliters to about 25 microliters per kilogram of body weight per day.

12. The method of claim 9 wherein said Product R is administered in amount of about 15 microliters per kilogram of body weight per day for two weeks, and then 7.5 microliters per kilogram of body weight per day thereafter.

13. A method for treating a patient suffering from anemia resulting from chemotherapy, comprising administering parenterally to said patient an effective treatment amount of Product R in a sterile injectable formulation.

14. The method of claim 13 wherein said Product R is administered in a range from about 2.5 microliters to about 40 microliters per kilogram of body weight per day.

15. The method of claim 13 wherein said Product R is administered in a range from about 5 microliters to about 25 microliters per kilogram of body weight per day.

16. The method of claim 13 wherein said Product R is administered in amount of about 15 microliters per kilogram of body weight per day for two weeks, and then 7.5 microliters per kilogram of body weight per day thereafter.

17. A method of treating a patient suffering from anemia resulting from AIDS, comprising administering parenterally to said patient an effective treatment amount of Product R in a sterile injectable formulation.

18. The method of claim 17 wherein said Product R is administered in a range from about 2.5 microliters to about 40 microliters per kilogram of body weight per day.

19. The method of claim 17 wherein said Product R is administered in a range from about 5 microliters to about 25 microliters per kilogram of body weight per day.

20. The method of claim 17 wherein said Product R is administered in amount of about 15 microliters per kilogram of body weight per day for two weeks, and then 7.5 microliters per kilogram of body weight per day thereafter.

* * * * *